United States Patent [19]

Koning et al.

[11] Patent Number: 4,730,619

[45] Date of Patent: Mar. 15, 1988

[54] APPARATUS AND METHOD FOR ADJUSTING HEART/PACER RATE RELATIVE TO EJECTION TIME TO OBTAIN A REQUIRED CARDIAC OUTPUT

[75] Inventors: Gerrit Koning, Vries, Netherlands; Edward A. Schroeppel, Miamar, Fla.

[73] Assignee: Telectronics, N.V., Antilles, Netherlands

[21] Appl. No.: 924,764

[22] Filed: Oct. 30, 1986

Related U.S. Application Data

[63] Continuation of Ser. No. 722,574, Apr. 11, 1985, abandoned.

[51] Int. Cl.$^4$ .............................................. A61N 1/36
[52] U.S. Cl. ........................... 128/419 PG; 128/419 P
[58] Field of Search ...................... 128/419 PG, 419 D

[56] References Cited

U.S. PATENT DOCUMENTS

| | | | |
|---|---|---|---|
| 4,202,339 | 5/1980 | Wirtzfeld et al. | 128/419 PG |
| 4,291,699 | 9/1981 | Geddes et al. | 128/419 D |
| 4,446,872 | 5/1984 | Marsoner et al. | 128/700 |
| 4,456,013 | 6/1984 | DeRossi et al. | 128/674 |
| 4,535,774 | 8/1985 | Olson et al. | 128/419 PG |

OTHER PUBLICATIONS

"Rate Responsive Pacing Using the Evoked QT Principle, A Physiological Alternative to Atrail Synchronous Pacemakers", PACE, vol. 6, Nov.-Dec., 1983, pp. 1344-1349.

Primary Examiner—William E. Kamm
Assistant Examiner—Timothy Keegan
Attorney, Agent, or Firm—Henry W. Collins; Thomas R. Vigil

[57] ABSTRACT

The apparatus for pacing a heart in accordance with the heart rate needed to produce a required cardiac output while the person is exercising, comprises a pacer adapted to be implanted in a human body and having a pulse generator and control circuitry (e.g. including a microprocessor) therein, a pacing lead adapted to be implanted in a right ventricle in a heart and having a distal electrode adapted to engage and supply pacing pulses to the apex of the right ventricle and a pressure sensor or impedance sensing electrode mounted in or on the lead. An algorithm and routine utilizing same are stored in the control circuitry (microprocessor) and are adapted to (a) relate right ventricular pressure to duration of contraction to determine ejection time and changes in ejection time or (b) to relate impedance and changes in impedance to blood volume or changes in volume, to relate blood volume and changes in blood volume to opening and closing of the pulmonary valve and to determine each time period between each opening and closing to determine ejection time and changes in ejection time and to correlate ejection time or changes in ejection time with the required heart rate needed to supply a desired cardiac output and to cause the pacer to pace the heart at the required heart rate when the heart is not naturally paced.

33 Claims, 15 Drawing Figures

APPARATUS AND METHOD FOR ADJUSTING HEART/PACER RATE RELATIVE TO EJECTION TIME TO OBTAIN A REQUIRED CARDIAC OUTPUT

This is a continuation of application Ser. No. 722,574 filed Apr. 11, 1985, now abandoned.

BACKGROUND OF THE INVENTION

1. Field of the Invention

The present invention relates to a pacer system which is adapted to alter the rate of pacing pulses delivered by an artificial pacemaker to a heart while an individual is exercising utilizing ejection time to obtain a required cardiac output.

2. Description of the Prior Art

Heretofore patients with heart dysfunctions or heart disease such as sinus node disease have been able to live a relatively normal life with the implantation of an artificial pacemaker often referred to as a pacer. However, such pacers have not always been able to mimic the response of a normal healthy heart. A normal heart responds to exercise and stress by increasing cardiac output through increased heart rate or stroke volume.

In this respect, patients with sinus node disease have lost the ability to increase heart rate with exercise. Accordingly, it has become a goal of optimal pacing to provide exercise responsiveness in a pacer by sensing the need for increased cardiac output.

With a view toward obtaining this goal, a number of pacemakers have been proposed for indirectly sensing the need for increased heart rate by sensing P-waves, nerve impulses, Q-T interval, pH, oxygen saturation, respiratory rate, stroke volume, motion, atrial pressure and temperature.

A P-wave triggered artificial pacemaker adapted to be exercise responsive by responding to average atrial rate has been proposed in the Knudson & Amundson U.S. Pat. No. 4,313,442.

An artificial pacemaker responsive to changes in the Q-T interval is proposed in the Rickards U.S. Pat. No. 4,228,803.

The Heilman et al. U.S. Pat. No. 4,303,075 discloses a method and apparatus for maximizing stroke volume through AV pacing using an implanted cardioverter/pacer which is programmed with an AV delay tailored to the particular patient. The mechanism detects and processes the impedance of the heart across two electrodes in contact with heart muscle during each heart cycle and uses the changes from cycle to cycle to trigger the issuance of pulses from the pacer depending on the direction of the impedance changes to maximize stroke volume of the heart, which is proportional to the change in value of impedance between the minimum and maximum detected impedance per heart cycle.

The Funke U.S. Pat. No. 4,312,355 discloses a dual pace-dual sense cardiac pacer which is able to stimulate the atrium and/or the ventricle and which is able to entrain the ventricle, when the atrial rate increases, while preventing bradycardic episodes. The pacer action is triggered by detection of naturally occurring atrial and ventricular action or pulses within a predetermined time period.

The Roline U.S. Pat. No. 4,363,325 discloses a multiple mode pacer activated to switch modes relative to heart rate thereby preventing atrial bradycardia. This is achieved by mode switching of the pacer from an atrial synchronous mode to a ventricular inhibited mode. Such switch of modes is actuated when no atrial activity is sensed within a preset escape interval referred to as a hysteresis period. Reversal of the mode back to the atrial synchronous mode from the ventricular inhibited mode is actuated in response to a detected atrial rate which is higher than a preset, lower, ventricular rate. With this mode switching, the ventricle will not be stimulated twice in quick succession, which overstimulation could cause atrial bradycardia.

A proposal for placing electrodes on the Hering's nerve that extends from receptors in the sinus and glomus carotids is disclosed in the Gonzalez U.S. Pat. No. 4,201,219.

Sensors for sensing blood pH are proposed in the Alcidi U.S. Pat. No. 4,009,721 and the Mauer et al U.S. Pat. No. 4,252,124. Alcidi controls a pacer relative to blood pH.

In the Bornzin U.S. Pat. No. 4,467,807 molecular oxygen is sensed with an oxygen sensor, preferably of the type as disclosed in the Wirtzfeld et al U.S. Pat. Nos. 4,202,339 and 4,299,820. The Wirtzfeld et al patents teach measuring of oxygen saturation of blobd using optical techniques. The transmissiveness of light through blood is used by Wirtzfeld et al to measure oxygen concentration. Bornzin teaches using such measurements for controlling the pacing of a heart.

An artificial pacemaker that senses oxygen saturation at the tip of a catheter in the right ventricle is proposed in the Wirtzfeld et al U.S. Pat. No. 4,202,339.

Another artificial cardiac pacemaker which increases pacing rate in accordance with an increase in respiration rate is proposed in the Krasner U.S. Pat. No. 3,593,718.

Pacers for sensing motion or mechanical activity are proposed in the Dahl U.S. Pat. No. 4,240,132 and the Anderson et al U.S. Pat. No. 4,428,378.

The Denniston III U.S. Pat. No. 3,815,611 discloses an apparatus which detects muscle contractions through impedance measurement. The device includes an elastomer body whose impedance changes when flexed. The elastomer body is positioned adjacent a muscle such as a heart muscle such that when the muscle contracts, the elastomer body is flexed to provide a change in impedance to a bias voltage supplied thereto. Such electrical signal can be used to control a pulse generator to generate a pulse when a specified period of time has elapsed since the latest heart activity was sensed by the elastomer body.

Another artificial cardiac pacemaker responsive to exercise by sensing venous blood temperature in the right ventricle of the heart is proposed in the Cook et al U.S. Pat. No. 4,436,092.

In a healthy heart, the sympathetic nervous system activates the sinus node to increase its rate. Secondly, it activates the heart to increase its dynamic contraction during exercise. The first activation is lost in patients with sinus node disease but the second phenomenon of dynamic contraction still exists. This means that exercise modified increased sympathetic activity can be detected by measuring the changes in the ejection time in the right ventricle. As will be described in greater detail hereinafter, the apparatus and method of the present invention utilizes changes in the ejection time in the right ventricle to control the pacing rate of an implanted artificial pacemaker.

Heretofore it has been proposed in the Cohen U.S. Pat. No. 3,358,690 to sense pressure in the right atrium and to utilize the pressure sensed to control pacing of an electrode in the right ventricle.

Also, the Zacouto U.S. Pat. No. 3,857,399 discloses, in FIG. 19 thereof, a pressure sensor that measures either left ventricular pressure or intramyocardial pressure. One sensor is located in the myocardium or septum and the other sensor is located in the left ventricle. Apparently, the pacer coupled to these sensors responds to average base pressure over relatively long periods of time and the pacer system disclosed therein appears to be static and slowly responsive to exercise.

The Sjostrand et al. U.S. Pat. No. 3,650,277 discloses a system for reducing and controlling the blood pressure of a hypertensive patient by electrical stimulation of the carotid sinus nerves, one of the baroreceptor centers of the body. The system incorporates a pressure transducer which is connected to or applied to an artery of a patient and provides electrical signals substantially representing the instantaneous arterial blood pressure of a patient. Upon calculation of a mean arterial pressure, the system is utilized to provide a series of electrical pulses having a predetermined frequency, magnitude and amplitude through an afferent nerve, such as the carotid sinus nerve, to the heart to mimic pulses to the heart occurring naturally in patients having normal blood pressure. These pulses are provided during the first portion of each heart cycle to take over the function of controlling blood pressure that is usually provided by normally functioning baroreceptors in patients who are not hypertensive.

In the field of artificial hearts, it has been proposed in the Purdy U.S. Pat. No. 3,828,371 directed to a self contained artifical heart, to control the operation of an artificial heart relative to the sensing of atrial pressure.

Further, there is disclosed in U.S.S.R. Inventor's Certificate No. 858,843 a device for controlling a prosthesis of the heart which replaces a natural heart and pressure in the atrium of the heart.

The apparatus of the present invention can utilize a pressure sensor for sensing right ventricular pressure changes for determining ejection time as well as changes in ejection time. The pacer rate is adjusted relative to changes in ejection time. Further, a number of different pressure sensors, including piezoresistive pressure sensors, can be used to sense the right ventricular pressure. See for example the pressure sensors and transducers disclosed in the following U.S. patents:

| U.S. PAT. NO. | PATENTEE |
| --- | --- |
| 2,634,721 | Greenwood, Jr. |
| 2,976,865 | Shipley |
| 3,088,323 | Welkowitz et al |
| 3,038,465 | Allard et al |
| 3,294,988 | Packard |
| 3,563,245 | McLean |
| 3,906,960 | Lehr |
| 4,432,372 | Monroe |
| 4,456,013 | DeRossi et al |
| Published European Patent Application 0 080 347 to | Anderson et al |

In one embodiment of the apparatus of the present invention, changes in impedance between two spaced apart electrodes in the right ventricle can be used to determine ejection time as the blood content in the right ventricle changes during heart pumping activity. Then the changes in ejection time can be used to adjust the pacing rate.

In the article entitled "Continuous Measurement of Ventricular Stroke Volume by Electrical Impedance" by Geddes, Hoff, Mello and Palmer appearing in Vol. 4, No. 4 April–June 1966 issue of "Cardiovascular Research Center Bulletin" different techniques for measuring impedance in ventricles, particularly the left ventricle, for use in measuring ventricular stroke volume, are described.

Moreover, it has been proposed in the Geddes et al U.S. Pat. No. 4,291,699 to measure impedance by means of two electrodes in a right ventricle when electrical analysis indicates that ventricular fibrillation is present and persists. The impedance measurements are then used to determine mechanical pumping activity of the heart. A defibrillator is actuated only when both mechanical and electrical activity of the ventricle indicate a need for defibrillation.

The apparatus of the present invention differs from the previously proposed apparatus and methods by providing an implanted artificial pacemaker having a microprocessor therein with a program or algorithm stored in the microprocessor for controlling the pacing rate of pacing pulses supplied to an electrode at the end of a pacing lead in the right ventricle relative to, and in response to, the changes in the ejection time of the right ventricle as obtained by sensing the opening and closing of a pulmonary valve with sensing means mounted on the pacing lead and located in the right ventricle.

SUMMARY OF THE INVENTION

According to the present invention, there is provided an apparatus for pacing a heart in accordance with the heart/pacer rate needed to produce a required cardiac output while the person is exercising, comprising:

a pacer adapted to be implanted in a human body and having a pulse generator and control circuitry which may be realized by a microprocessor therein;

a pacing lead adapted to be implanted in a heart and having a tip electrode adapted to engage and supply pacing pulses to a right ventricle of a heart;

means for determining the duration of contraction of the heart to determine the ejection time and changes in ejection time over time in the right ventricle; and means, including said control circuitry for relating the changes in ejection time with the required pacing rate needed to supply a desired cardiac output and for causing said pacer to pace the heart at the required rate when the heart is not naturally paced.

Further according to the invention, there is provided a method for pacing a heart in accordance with the heart rate needed to produce a required cardiac output while the person is exercising, comprising the steps of determining ejection time and changes in ejection time in the right ventricle;

relating ejection time and/or the changes in ejection time with the required heart rate needed to supply a desired cardiac output; and pacing the heart at the required heart rate when the heart is not naturally paced.

In the application of the apparatus one can measure pressure over a period of time and relate changes in pressure to the duration of contraction. Changes in the duration of contraction caused by exercise tend to parallel changes in ejection time which is the time period between opening and closing of a pulmonary valve. As a result, changes in duration of contraction and therefore ejection time can be determined and related to pacer rate for determining the pacer rate at which pulses are required.

In another application of the apparatus, one can measure changes in blood impedance in the ventricle which are related to the volume of blood in the ventricle. The impedance measurement is utilized to calculate blood volume changes in the ventricle. Then the changes in blood volume can be used to determine opening and closing of a pulmonary valve. Next, the time period between opening and closing of the pulmonary valve can be determined, which is ejection time. Changes in this time period can then be determined and related to pacer rate. Then this pacer rate is compared with the patient's heart rate to determine if pacing pulses are required and at which rate.

DESCRIPTION OF THE PREFERRED EMBODIMENTS

Figure 1:
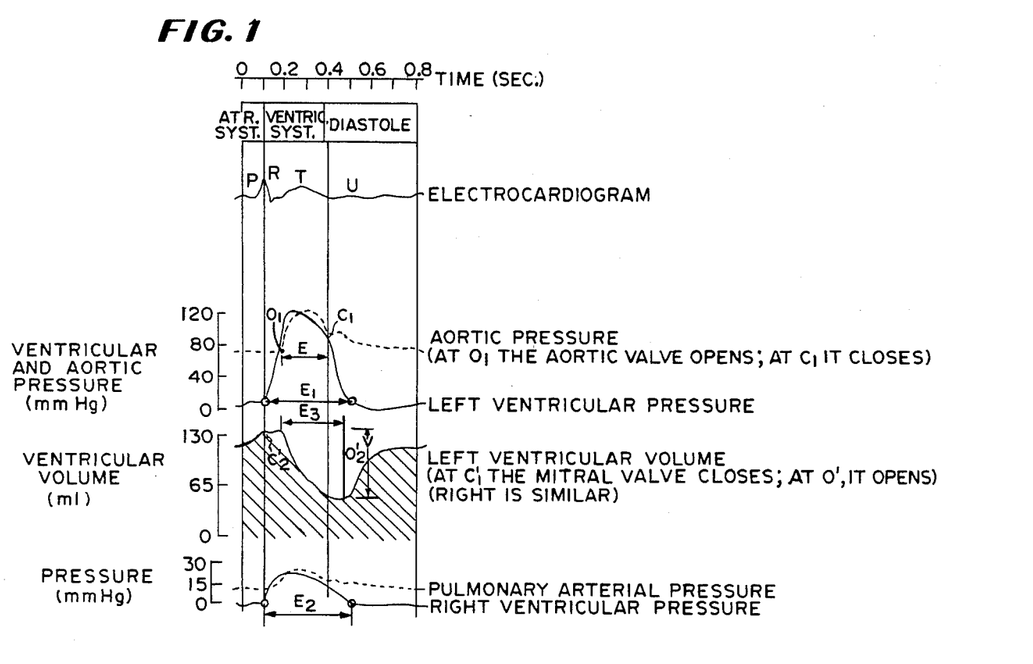
FIG. 1 is a set of graphs of various parameters of heart activity versus time from atrial systole through ventricular systole to diastole.

Referring now to FIG. 1, there is illustrated therein a graph of various parameters of heart activity versus time from atrial systole through ventricular systole to diastole. From this graph it will be appreciated that various phenomena occur during heart activity. In this respect, there are changes in aortic pressure, left ventricular pressure, left ventricular volume (right ventricular volume as well) and right ventricular pressure. The changes in these parameters are indicative of ejection time. Here, for example, the change in aortic pressure from $0_1$ to $C_1$ is a measure of ejection time E.

A measure of duration of contraction is the change in left ventricular pressure which is shown as $E_1$ in FIG. 1 and which is proportional to ejection time. In this respect, when the contraction starts the pressure increases until it reaches the aortic pressure then the aortic valve opens and blood is ejected from the left ventricle. After some time the pressure decreases to a value lower than the aortic pressure at the time the aortic valve closes. The time period between opening and closing of the aortic valve is called ejection time. Again, the duration of contraction is shown as $E_1$, in FIG. 1, which is proportional to ejection time.

The same phenomenon occurs in the right ventricle. That is to say the pressure in the right ventricle is at a minimum, or 0. When contraction starts, the pressure starts to increase and the pulmonary valve opens when the pressure exceeds pulmonary pressure. It reaches a maximum and then decreases until all the blood is ejected from the right ventricle at which time the pulmonary valve closes and the pressure again returns to a minimum or 0. The time period between the opening and closing of the pulmonary valve is referred to as the ejection time of the right ventricle which is proportional to the duration of contraction $E_2$ of the right ventricle.

Another measure of ejection time is the time period in the left ventricle or in the right ventricle when the volume of blood in the right ventricle or left ventricle changes from a maximum value to a minimum value.

The time period during this change is equal to ejection time and is indicated as $E_3$ in FIG. 1.

As will be described hereinafter in greater detail, one can measure the continuous value of one parameter in the right ventricle and use the changes in that parameter to make determinations of ejection time $E_3$ and from the ejection times measured, determine changes in ejection time. Then changes in ejection time ($\Delta ET$) can be related to corresponding normal changes in heart rate ($\Delta HR$).

Figure 2:
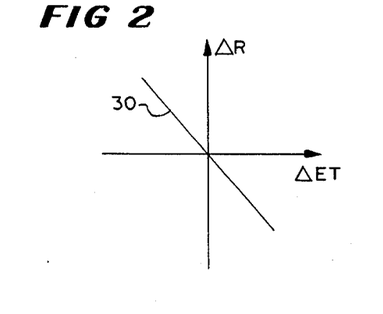
FIG. 2 is a graph of the change in pacer rate versus the change in ejection time, such as occurs during exercise.

The relationship of $\Delta ET$ to $\Delta R$ is shown in FIG. 2 and has been found to be a substantially linear relationship. Thus, in a normal heart, as changes in ejection time occur, changes in heart rate also occur.

With this observation, and according to the teachings of the present invention, one can sense changes in ejection time and then sense whether or not the pacemaker in the heart is adjusting the pacing rate $\Delta R$ in accordance with the graph shown in FIG. 2. If the natural pacemaker is not functioning properly, and such functioning is monitored by an implanted pacer system together with monitoring of ejection time, the pacer system can be caused automatically to output pacing pulses at the appropriate rate as determined by the ejection time and changes in the ejection time.

Figure 3:
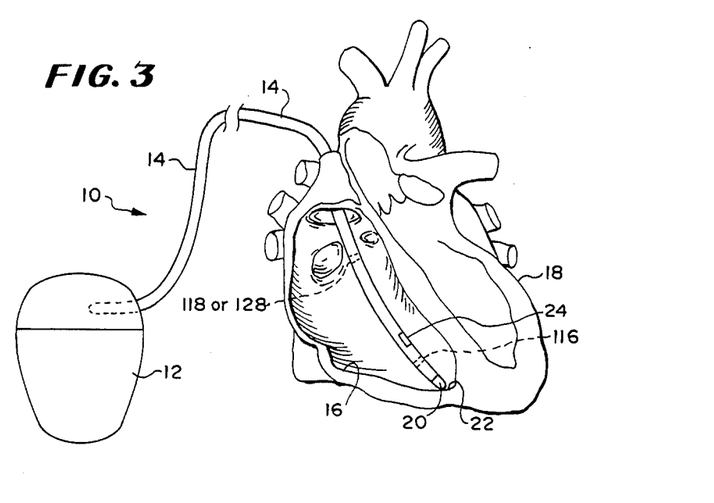
FIG. 3 is a side elevational view of a pacer and heart with portions broken away and with a pacing lead received in the right ventricle of the heart.

In FIG. 3 is illustrated an apparatus 10 or pacer system 10 which is constructed according to the teachings of the present invention and which includes an implanted pacer or artificial pacemaker 12. The pacer 12 has a pulse generator therein and associated cardiac excitation and cardiac activity detection circuitry as well as control circuitry.

The pacer 12 is connected to a pacing lead 14 at the proximal end thereof. The pacing lead extends pervenously into the right ventricle 16 of a heart 18 where a tip electrode 20 at the distal end thereof engages the apex 22 of the right ventricle for detecting cardiac activity and for stimulating the right ventricle 16.

A pressure sensor 24 is also mounted on the lead 14 and located in the right ventricle just above the tip electrode. The sensor can be connected to sensor amplifiers and detection circuitry in the pacer 12 as will be described in greater detail hereinafter.

The pacer system 10 controls the pacing rate of the pacer 12 relative to ejection time of the right ventricle as determined from determinations of duration of heart contraction.

When a patient with sinus node disease has a pacing system implanted within his or her body with the pacing lead 14 implanted in a ventricle of the heart, particularly the right ventricle, such pacing system 10 stimulates the ventricle through the tip electrode 20 at a preset rate. In patients with sinus node disease the heart has lost the ability to increase ventricular rate with exercise. However, the heart continues to increase its dynamic contraction.

In accordance with the teachings of the present invention, the right ventricular pressure is continuously sensed by the pressure sensor 24 and this pressure and changes in the pressure sensed are used for determining the duration of contraction. From the duration of contraction, changes are determined which parallel changes in ejection time. Then changes in ejection time coupled with sensing of heart activity are used to control the rate of application of pulses to the electrode 20, which rate is referred to as the pacer rate.

In other words, the continuous change in right ventricular pressure is used to determine the duration of contraction, changes in duration of contraction, ejection time and changes in ejection time over time which are then used as a measure of exercise level. Every exercise level has its corresponding heart rate. Thus, based on the ejection time or changes in ejection time over time related to exercise level, the appropriate heart/pacer rate can be determined. In this way, a pacer 12 can be adapted to exercise. More specifically, the rate of pulse generation or pacer rate can be controlled so that the pacing system 10 can be adapted relative to ejection time and changes in ejection time over time for exercise when an individual engages in exercise.

Thus, it will be appreciated that the frequency of the heart rate of a normal heart can be correlated to right ventricular ejection time and changes in ejection time over time as determined by continuous measurement of the right ventricular pressure over time while an individual is exercising and such correlation is generally linear as shown by the slope 30 of the graph of changes in ejection time, $\Delta ET$, versus changes in heart rate or pacer rate, $\Delta R$, as shown in FIG. 2.

As will be described in greater detail hereinafter, this relationship between the change in ejection time as determined from changes in right ventricular pressure to the change in heart rate for a normal heart can be programmed in the form of an algorithm in the memory of the microprocessor or any other control circuitry mounted within the pacer 12. Thus, in one embodiment of the apparatus or pacing system 10 one can utilize the changing pressure sensed by the pressure sensor 24 in the right ventricle to adjust the pacer rate according to the algorithm stored in the memory of the microprocessor within the pacer 12 which relates changing right ventricular systolic pressure to ejection time and changes therein to determine the required rate of heart contractions or pacer rate.

For this purpose, the system 10 requires the pressure sensor 24 in the implanted pacing lead 14 and the electronic circuitry in microprocessor based pacer 12 for calculating the required change in rate based on the pressure change and the algorithm stored in the memory to cause the control circuitry to change the pacer rate.

It may be preferable to use changes of the ejection time, $\Delta ET$, instead of the ejection time, ET, itself. For this purpose, the pacer 12 will have a differential circuit or algorithm incorporated therein. Use of the changes in the ejection time signal avoids DC drift because $\Delta ET$ is an AC signal.

It will be appreciated that the measure of ejection time referred to above is the ejection time of the right ventricle, which is derived from the duration of contraction, $E_3$ in FIG. 1, which is determined from changes in right ventricular pressure.

The pressure sensor 24 can be defined or realized by a number of different types of pressure sensing elements. For example, the pressure sensor may be a hermetically sealed absolute strain gauge transducer or a piezoresistive transducer. Also a fiber optic type pressure sensor can be utilized.

Figure 4:
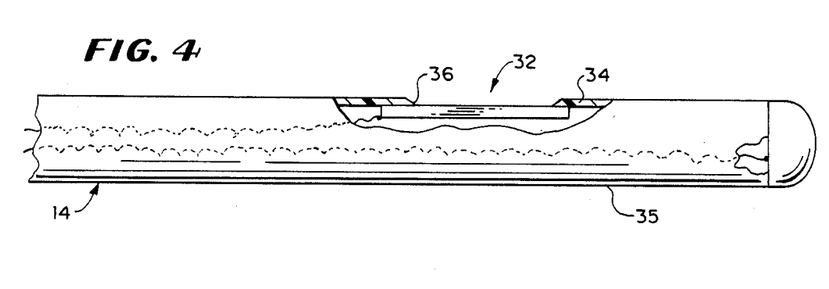
FIG. 4 is a longitudinal plan view with portions broken away of one embodiment of a distal end portion of a pacing lead assembly which has a piezoresistive pressure sensor mounted thereon and which can be used in the apparatus of the present invention.

In one preferred embodiment of the apparatus 10 of the present invention, the pressure sensor 24 is realized by a piezoresistive microelectronic transducer 32 which is fixed within or on the inside of a wall 34 of a tubular sheath 35 of the lead 14 beneath an opening 36 in the sheath 35 as best shown in FIG. 4.

The transducer 32 can be mounted on a glass carrier and four wire conductors are then coupled to the glass carrier for connection to the transducer 32. The four wire conductors are connected to a bridge comprised of variable piezoresistors of the transducer 32.

As is typical of piezoresistive transducers, the transducer 32 comprises the four resistors electrically connected in the bridge circuit. A voltage is applied across two corners of the bridge via two sensor wire conductors. Then, the voltage across the other two corners of the bridge is sensed, i.e. by the voltage across the other two sensor wire conductors.

Initially, without any pressure placed on the transducer 32 the voltage will be zero. However, when pressure is placed on the transducer 32, the resistance of two resistors will go down and the resistance of the other two resistors will go up. This will cause a change in the value of the voltage across the other two corners of the bridge which voltage is supplied via two sensor wire conductors to the pacer 12 of the apparatus 10 as an indication of a change in right ventricular systolic pressure.

Typically, a pressure sensor 24 having an impedance of approximately 1 k ohm requires 1–5 Volt excitation which translates to approximately 1–5 mA current flow. One to five mA is too much current drain for the battery power source for the pacemaker 12. Accordingly, to reduce the current drain, voltage and current pulses with a 1:200 duty cycle are utilized and supplied to and received from the bridge circuit whereby the current drain is reduced to an acceptable value of approximately 5 microamps. In this way, with voltage pulses having a duty cycle of 1:200 the pressure applied to the transducer 32 of the pressure sensor 24 is only sampled periodically. Then, of course, the sampling frequency relative to pulse duration has to be chosen in such a way as to minimize current drain and still yield a reproducible pressure curve such as by utilizing the Shannon-Nyquist theorem of sampling.

At the onset of exercise, the right ventricular systolic pressure will vary with heart rate or pacer rate. The first step in utilizing the apparatus 10 involves sensing of changes in the right ventricular pressure.

To avoid small oscillations a general filtering principle or an N-point averaging technique is employed. In this respect, an N number of samples between 1 and 10, for example, are made and the average is chosen as the sampled pressure, P. Then, this average is compared with the previously stored average of the pressure value to determine whether there has been a change. The change is detected by measuring $\Delta P = P_x - (P_{x-1})$ where x equals the time order for a number of samples, N. Of course, to make this detection more reliable, one would detect, sense and determine $P_x - (P_{x-1})$, $(P_{x-1}) - (P_{x-2})$ and $(P_{x-2}) - (P_{x-3})$. As a simplification, when all the differences have the same sign, the change is consistent. Then $\Delta P = P_x - (P_{x-1})$ and that is stored in the microprocessor within the pacer 12. Then from changes in pressure and particularly determinations of when the pressure starts to increase from a minimum or zero and decreases to and stops at a minimum or zero, the microprocessor can determine duration of contraction and therefore ejection time. Subsequently changes in ejection time are determined for use in calculating the desired heart/pacer rate and, if necessary, to initiate pacing pulses to maintain a desired pacer rate.

Figure 5:
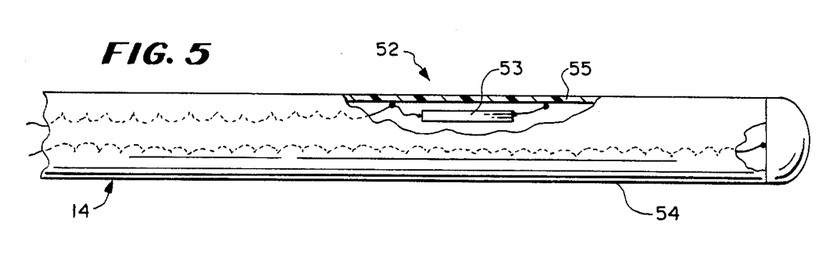
FIG. 5 is a longitudinal plan view with portions broken away of another embodiment of a distal end portion of a pacing lead which has a strain gauge pressure sensor mounted thereon and which can be used in the apparatus of the present invention.

In FIG. 5 is shown a transducer 52 comprising a strain gauge 53 mounted within a tubular sheath 54 of a pacing lead 14 and secured to the wall 55 of the sheath 54. Bending of the lead by contraction determined by the strain gauge 53 is then used to determine duration of contraction and therefore ejection time and changes in ejection time. Bending of the lead by contraction can also be measured by a piezo crystal or any other piezoelectric material. This has the advantage that contrary to a pressure transducer or a strain gauge, this type of sensor material does not require an excitation voltage but generates its own output voltage.

The algorithm or routine in its simplest form relates $\Delta R$, which is the change in rate of pulses emitted by the pacer 12, to $\Delta ET$, which is the change in ejection time. This can be realized in analog techniques but can also be realized in a digital manner using a so-called "look-up" table. The signal $\Delta P$ serves as an input to the microprocessor in the pacer 12 for calculating ejection time ET and to determine $\Delta ET$ for changing the pacer rate frequency as a function of $\Delta ET$. Typically, an algorithm relationship of $\Delta ET$ to $\Delta R$, such as shown in FIG. 2, is stored in the memory of the microprocessor in the pacer 12 and provides the algorithm, i.e., slope 30, and the equation therefor, which is utilized by the control circuitry.

In the event the sensor 24 or the circuitry within the pacer 12 malfunctions, the control circuitry can be caused to exit the program or routine and convert the pacer to its standard non-exercise responsive function. Furthermore, if the pressure shows oscillation without exercise, the number N in the N-point averaging can be programmed or changed to a higher value and the circuitry for sensing or detecting a change in pressure can be programmed to take more samplings of differences before it decides that a change in pressure, $\Delta P$, has occurred.

The advantage of utilizing duration of contraction or ejection time of the right ventricle resides in the fact that the change in right ventricular pressure is directly proportional to the sympathetic nerve activity and exercise activity. That is to say, in a normal human being, right ventricular contraction duration and right ventricular ejection time changes appear to be inversely proportional to exercise without any time lag. This has an advantage over metabolic changes such as pH, oxygen saturation, etc., all of which occur at a time subsequent to the onset of exercise. Therefore, by utilizing the right ventricular pressure to determine ejection time, a pacer directly follows exercise rather than lagging exercise.

Figure 6:
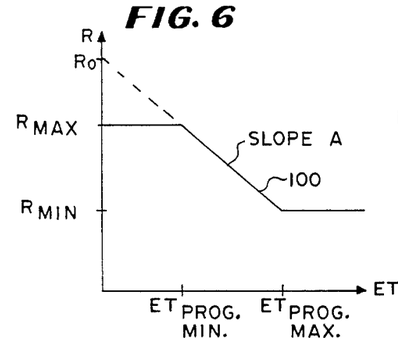
FIG. 6 is a graph of pacer rate versus ejection time and shows the linear relationship between the pacer rate and the ejection time between programmed minimum and maximum rates.

In utilizing the apparatus 10 as shown in FIG. 3, certain parameters have to be determined experimentally and programmed into the microprocessor within the pacer 12. First of all, as shown in FIG. 6, the linear relationship between heart rates and right ventricular ejection times between a programmed minimum rate, $R_{Min.}$, and a programmed maximum rate, $R_{Max.}$, of heart rates is established and can be shown as graph or line 100 having a slope, "A". The equation for the line 100 with the slope "A" is:

$$R_T = (R_{T-1}) - A(ET_T - ET_{T-1})$$

Figure 7:
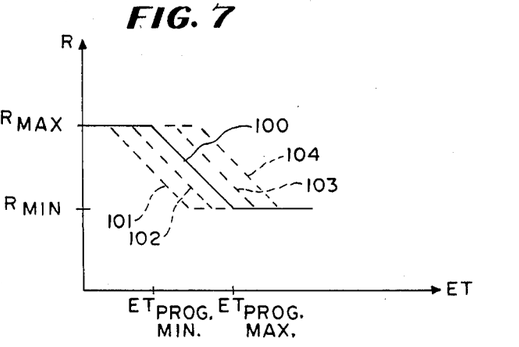
FIG. 7 is a graph of pacer rate versus ejection time and shows a family of lines or slopes along which a pacer can function and shows that the rate of change is a function of the difference between ejection time at one point in time and ejection time at another point in time and not of their absolute value.

In FIG. 7, a number of lines 101–104 parallel to and on either side of the line or graph 100 are programmed in the microprocessor so that the pacer 12 can function along the family of lines 100–104. In this way, the minimum ejection time at which rate changes start can be programmed, which is essential because every patient has his/her own at rest ejection time. Note that this permits values of ejection time to be stored which are greater than $ET_{Prog.Max}$ and less than $ET_{Prog.Min.}$.

Additionally, for different patients one needs to determine the correct rate of change (or slope A) between ejection time, ET, and heart/pacer rate, R. In other words, such slope may be $A_1$ or $A_2$ for lines 106,108 as shown in FIG. 7A.

This formula or algorithm is then utilized in the routine or program carried out by the microprocessor in the pacer 12. This routine is set forth in the flow chart shown in FIG. 8. According to this routine, the heart pacing rate and ejection time values stored in the pacer 12 are constrained to vary along the line 100 (or 101, 102, 106 or 108) delineated by the above equation having the slope "A" (or $A_1$ or $A_2$) as determined for the patient. That is to say, even if the measured ejection time ET exceeds the programmed maximum ejection time, $ET_{Prog.Max.}$, that value of ET will be stated as $ET_{Prog.Max.}$. This is required because the pacer 12 has upper and lower pacing rate limits as set by the physician and the pacer 12 cannot go above or below these pacing rate limits.

Figures 7A, 8:
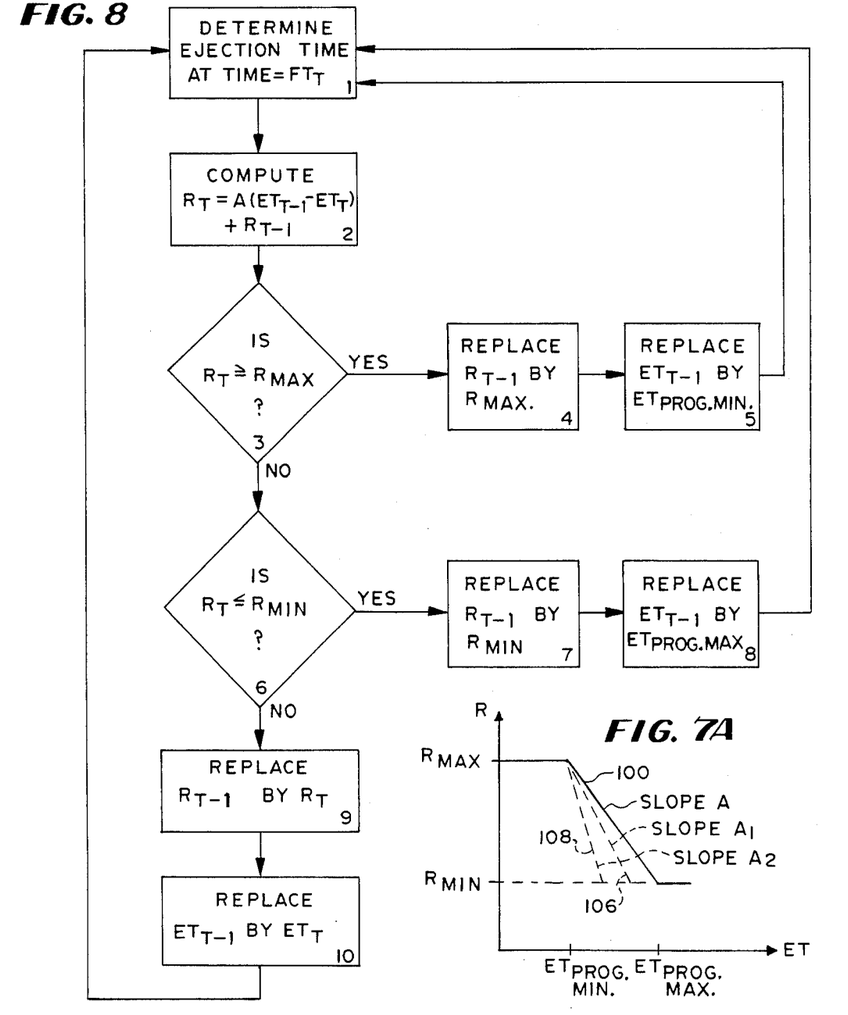
FIG. 7A is a graph of pacer rate versus ejection time for different rates of change (slope) of pacer rates relative to ejection times for different patients.
FIG. 8 is a flow chart of the program or routine carried out by the microprocessor of the apparatus shown in FIG. 3.

The steps carried out by the program or routine shown in FIG. 8 are as follows:

STEP 1. Here after pressure values and changes in pressure values have been measured ejection time is determined at a starting time T and defined as $ET_T$.

STEP 2. Here $R_T$ is calculated. If $(ET_{T-1}) - ET_T$ is positive, $R_T$ will be larger than $R_{T-1}$. If negative, it will be smaller.

STEP 3. The pacer rate will only be changed to values on the sloped portion of the graph 100 as shown in FIG. 6. At STEPS 3 and 4, a determination is made whether or not the value for the pacer rate will be at the extremes of the line or graph 100.

STEP 4. If $R_T$ is equal to or greater than $R_{Max.}$, then the pacer is programmed to $R_{Max.}$ and this value is stored as $R_{T-1}$.

STEP 5. Next the stored ejection time is stored as $ET_{Prog.Min.}$ and the routine loops back to STEP 1.

STEP 6. If $R_T$ is less than $R_{Max.}$, then the program goes on to STEP 6 where it is determined whether or not $R_T$ is equal to or less than $R_{Min.}$.

STEP 7. If $R_T$ is equal to or less than $R_{Min.}$, the microprocessor is caused to program the pacer to $R_{Min.}$ and stores that value as $R_{T-1}$.

STEP 8. Next, $ET_{T-1}$ is stored as $ET_{Prog.Max.}$ in the memory of the microprocessor.

STEP 9. If the microprocessor reaches this step, it means that $R_T$ is somewhere on the sloped portion of the graph or line 100. The pacer is then programmed to $R_T$ and $R_{T-1}$ is replaced by $R_T$.

STEP 10. Next, at STEP 10, $ET_{T-1}$ is replaced by $ET_T$, and the microprocessor loops back to STEP 1.

It is to be noted that in most pacers the actual value programmed into a microprocessor would be the closest programmable value to $R_T$. However, $R_{T-1}$ is a calculated number. Again, after $R_{T-1}$ has been replaced by the closest programmable value of $R_T$ and $ET_{T-1}$ has been replaced by $ET_T$, the microprocessor returns to STEP 1 and continues to control pacing rate relative to ejection time.

Figures 9, 10:
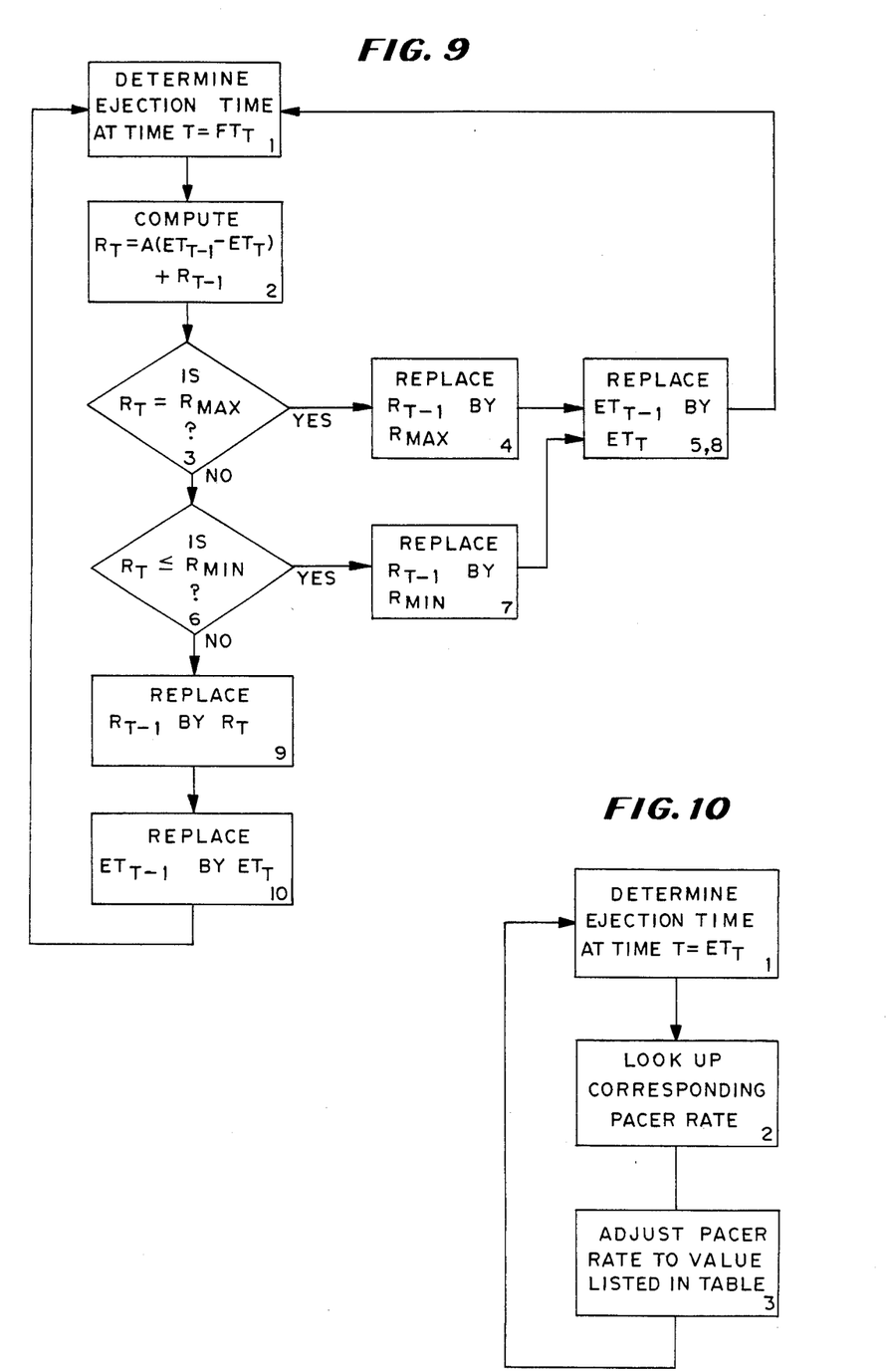
FIG. 9 is a flow chart of the program or routine carried out by the control circuitry (e.g. microprocessor) of the apparatus shown in FIG. 3. This program is modified from the flow chart shown in FIG. 8 to permit values of ejection time to be stored which are greater than the preprogrammed maximum ejection time and less than the preprogrammed minimum ejection time to establish the family of lines or slopes along which the pacer can function as shown in FIG. 7 so that the apparatus will not be sensitive to drift of a pressure sensor or an impedance measuring system.
FIG. 10 is a flow chart of a program or routine carried out by the control circuitry of the apparatus shown in FIG. 3 which uses a look-up table suitable for both linear and non-linear relationships between heart rate or pacer rate and ejection time.

In the flow chart shown in FIG. 9, the STEPS 1-10 are essentially the same as STEPS 1-10 in the flow chart shown in FIG. 8. However, STEPS 5 and 8 have been modified from STEPS 5 and 8 in the flow chart shown in FIG. 8 and this permits values of ejection time to be stored which are greater than $ET_{Prog.Max.}$ and less than $ET_{Prog.Min.}$.

For the mode of operation defined by the flow chart shown in FIG. 9, $ET_{Prog.Max.}$ and $ET_{Prog.Min.}$ have no meaning. This allows for sensor drift and movement of the lines or curves of the graph shown in FIG. 7.

In STEP 5 and in STEP 8 combined in FIG. 9, ET is stored as $ET_{T-1}$. Also, note that STEP 10 can be combined with STEPS 5 and 8 as shown in FIG. 9.

In FIG. 10 there is set forth a simple flow chart which utilizes a look-up table of right ventricular ejection time versus heart/pacer rate suitable for both linear and non-linear relationships between heart/pacer rate and ejection time.

The steps of this program or routine are as follows:

STEP 1. Here ejection time is determined.

STEP 2. Here the corresponding pacer rate is pulled from the look-up table stored in memory. Each ejection time or range of ejection time values has a corresponding rate which had previously been entered into the memory.

STEP 3. Here the pacer rate is adjusted or changed to that one found in the memory which corresponds to the ejection time determined.

After STEP 3, the microprocessor loops back to STEP 1 and continues to determine ejection time.

Figure 11:
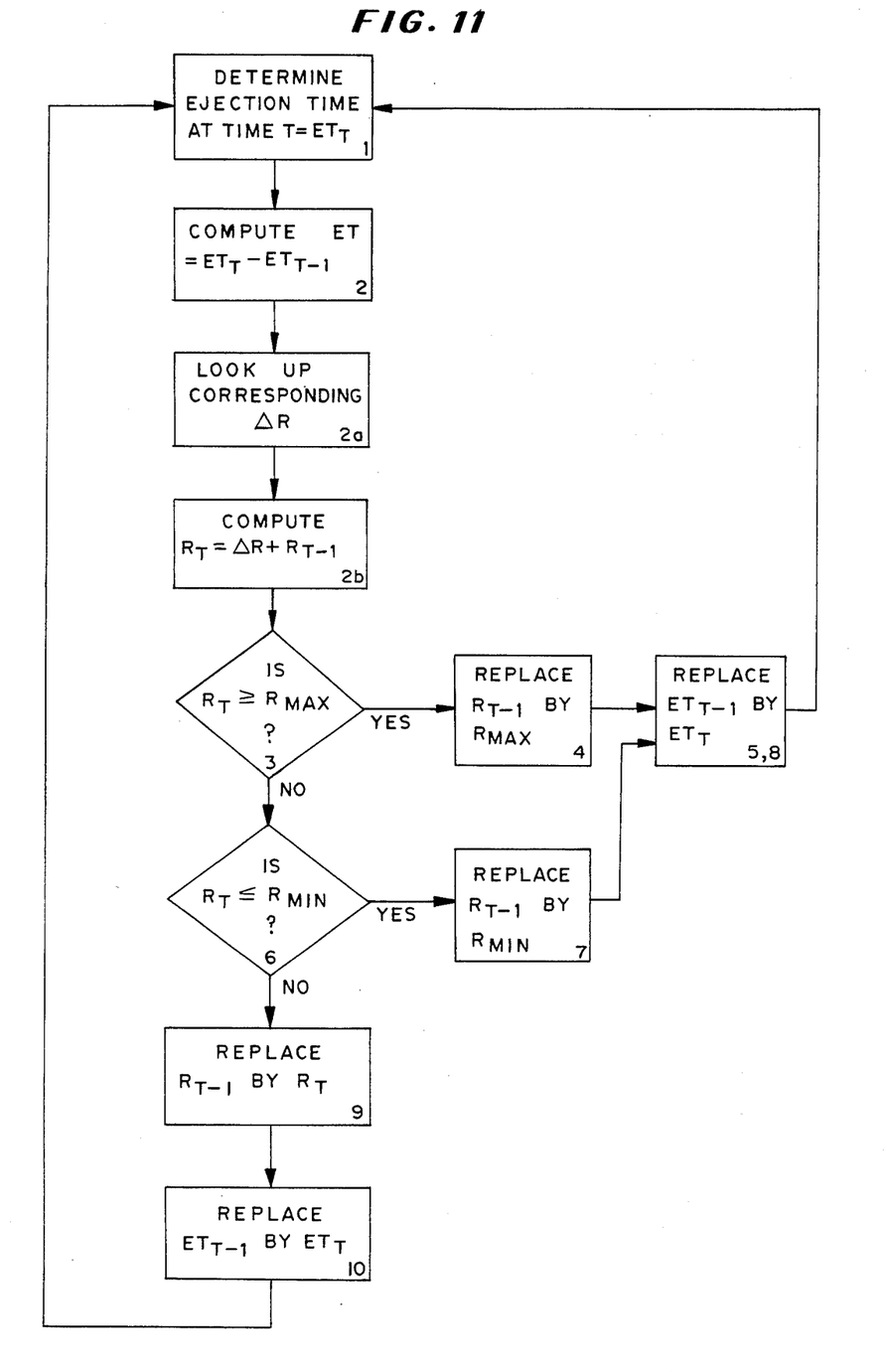
FIG. 11 is a flow chart similar to the flow chart shown in FIG. 9 of a program or routine carried out by the control circuitry of the apparatus shown in FIG. 3 using a look-up table for the change in ejection time and not the actual value of ejection time so that the apparatus will not be sensitive to drift of a pressure sensor or an impedance measuring system.

In FIG. 11 is illustrated a flow chart of another program or routine which is analogous to the routine and flow chart therefor shown in FIG. 9. In this routine, compensation for pressure sensor drift is provided by using a look-up table for the change in ejection time and not the actual value of ejection time as determined from changes in pressure (right ventricular pressure). The steps of this program are as follows:

STEP 1. Here the ejection time is measured at time T to determine $ET_T$.

STEP 2. Here the microprocessor computes $\Delta ET = ET_T - (ET_{T-1})$ which is the change in ejection time.

STEP 2a. Here the microprocessor looks up in the memory the corresponding pacer rate change, $\Delta R$ (which can be a function of $R_{T-1}$, the present rate).

STEP 2b. Here the microprocessor computes $R_T = \Delta R + R_{T-1}$.

STEPS 3-10. These steps are identical to STEPS 3-10 of the flow chart shown in FIG. 9.

In any one of the programs represented by the flow charts in FIGS. 8-11, the pacer rate changes may be smoothed by smoothing the changes in ejection time. This can be done in several ways.

One approach is to compute the sign of the result of $\Delta ET = ET_T - (ET_{T-1})$ when ET is measured and compare the sign (positive or negative) to the sign of the $N-1$ previously computed differences which have been stored in the memory. If no sign change has occurred in N consecutive samples, the algorithm proceeds to determine the appropriate rate change.

Figure 12:
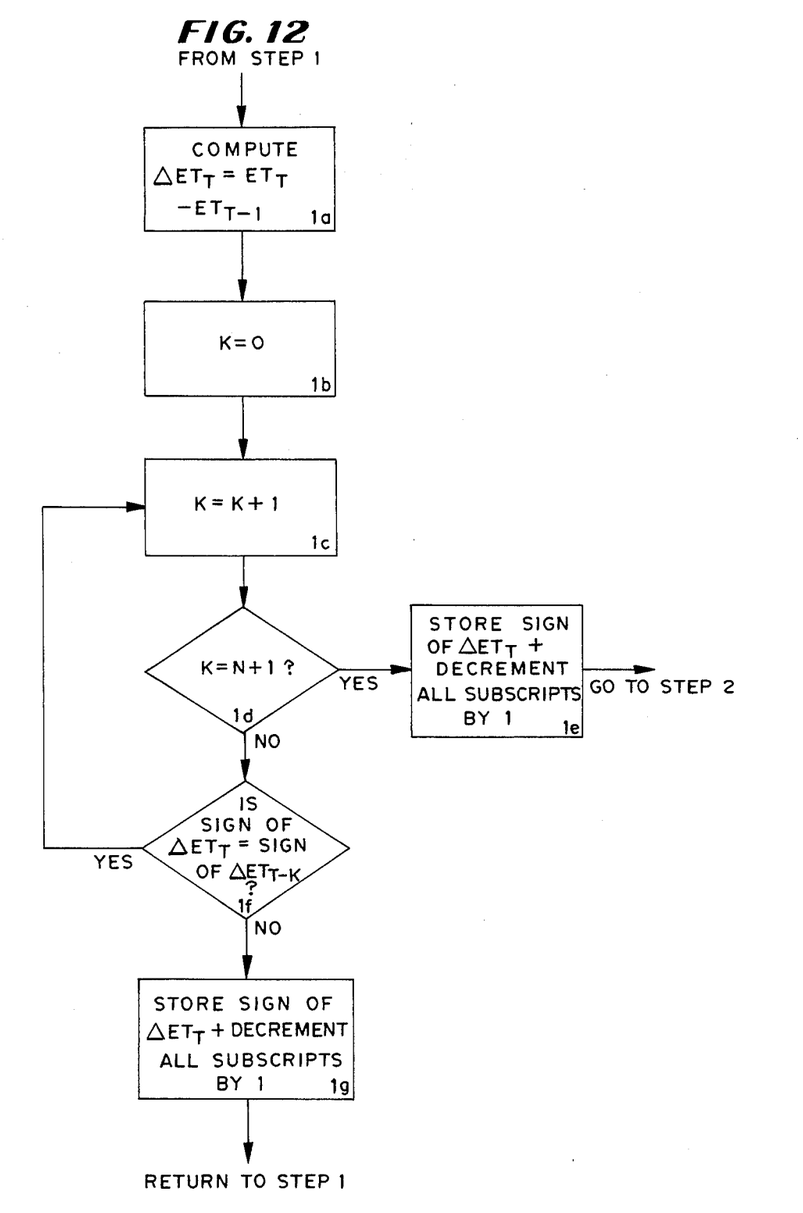
FIG. 12 is a flow chart of a subroutine that can be carried out by the control circuitry of the apparatus shown in FIG. 3 to provide smoothing of the heart rate changes by smoothing the changes in ejection time and is inserted between the first step and the second step of the routine or program shown in any one of FIGS. 8, 9, 10 and 11.

This is done with a subroutine shown in FIG. 12 which is inserted between STEPS 1 and 2 in any one of the flow charts shown in FIGS. 8, 9, 10 and 11. The steps followed in this subroutine are as follows:

STEP 1a. Here $\Delta ET$ is computed.

STEPS 1b-1d. These steps define a counting loop for indexing the subscripts of the previously calculated $\Delta ET$'s stored in the memory of the microprocessor starting with a count $K=0$.

STEP 1e. If $K=N+1$ at STEP 1d, at STEP 1e the sign of $\Delta ET_T$ is stored and all subscripts are decremented by 1. Then the microprocessor or algorithm carried out therein goes to STEP 2.

STEP 1f. If K≠N+1 at STEP 1d, at STEP 1f a determination of the sign of the present ΔET is made to see if it is equal to that of one of the previous N−1 ΔET's.

If the answer is yes, the microprocessor loops back to STEP 1c to increment ΔET for the next comparison.

STEP 1g. If the sign of the present ΔET is not equal to that of one of the previous N−1 ΔET's, the sign of the present ΔET is stored and all stored signs are moved down one level in the memory stack having a height N−1. Then the microprocessor returns to STEP 1.

Again, if N−1 comparisons have been made without any sign changes occurring such that the answer at STEP 1d is yes, at STEP 1e the sign of $\Delta ET_T$ is stored, the stack is moved down and the microprocessor proceeds to STEP 2 for an appropriate pacer rate change based upon $\Delta ET_T$.

Another approach to smoothing would be to use the subroutine shown in FIG. 12 except to change the pacer rate based upon the average value of ΔET over the N most recent samples if no sign change has occurred.

Figure 13:
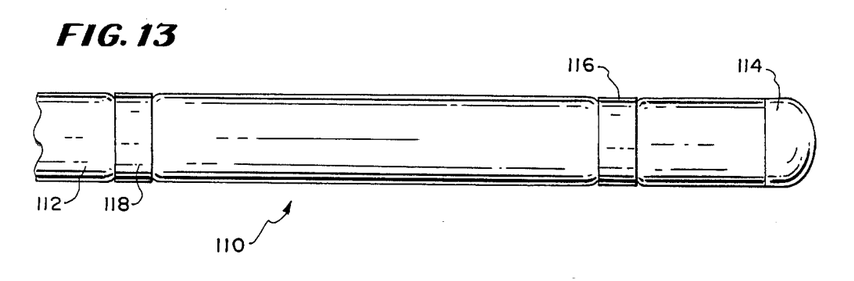
FIG. 13 is a longitudinal plan view of another embodiment of a distal end portion of a pacing lead which has a tip electrode and two spaced apart ring electrodes for measuring impedance in a right ventricle and which can be used in the apparatus of the present invention.

In FIG. 13 there is illustrated a distal end portion 110 of a pacing lead 112. The distal end portion 110 has a tip electrode 114 similar to the tip electrode 20 shown in FIG. 3.

The distal end portion 110 is further provided with a first ring electrode 116 which is spaced a short distance behind the tip electrode 114 and a second ring electrode 118 spaced further back from the first ring electrode 116. The ring electrodes 116 and 118, the tip electrode 114 and the pacer can 12 are utilized to measure impedance between the electrodes 116 and 118 through blood in a ventricle such as the right ventricle at any one of several frequencies by the so-called four electrode method. Current is injected between the pacer can 12 and the tip electrode 114. The voltage measured between ring electrodes 116 and 118 is then proportional to impedance. Then this measure of impedance is stored in the memory of the microprocessor and after a short period of time a second measurement is made. Changes in the impedance are indicative of and correlated to changes in volume of blood in the right ventricle. At the highest volume, the pulmonary valve opens and at the lowest volume the pulmonary valve closes.

The time of these points of high volume and low volume are noted and the difference in time is the ejection time. Then during exercise the ejection time will change and the changes in ejection time are utilized by the microprocessor in the pacer 12 to control the pacer rate determined by the ejection times determined, in the manner described above and as illustrated in FIGS. 8-12.

Figure 14:
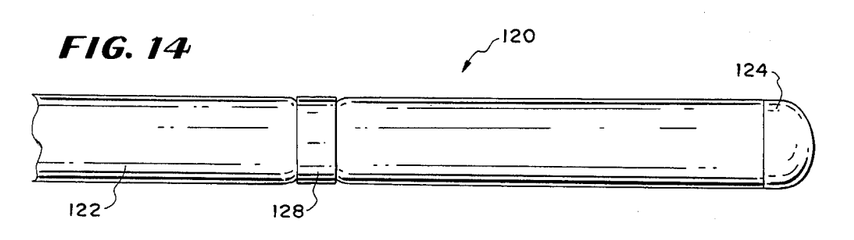
FIG. 14 is a longitudinal plan view, similar to the view shown in FIG. 13 but having only one ring electrode thereon such that impedance is measured between the tip electrode and the one ring electrode of still another embodiment of a distal end portion of a pacing lead.

To simplify the construction of the pacing lead used for measuring impedance, a distal end portion 120 of a pacing lead 122 can be formed in the manner shown in FIG. 14. Here a tip electrode 124 is provided and only one ring electrode 128 spaced a significant distance behind the tip electrode 124. The tip electrode 124 will still be used for supplying pacing signals to the apex of a ventricle while the ring electrode 128 is used with the tip electrode 124 for measuring impedance. A current at any one of several frequencies is injected between electrode 128 and tip electrode 124. At the same time the voltage between those electrodes 128 and 124 is measured and is proportional to impedance.

It will be appreciated that each of the electrodes for measuring impedance in the right ventricle, namely electrodes 116 and 118 or 124 and 128 are received in the ventricle as shown in phantom in FIG. 3. Also, the proximal ring electrode 118 and 128 will be disposed just beneath the tricuspid valve.

From the foregoing description, it will be apparent that the apparatus 10 of the present invention and the method for using same of the present invention enable one to adjust pacer rate in a pacing system relative to ejection time of the right ventricle during exercise with little or no time lag in the adjustment of the pacing rate relative to exercise level. The ejection time can be determined first by measuring pressure in the right ventricle at different points in time and determining the time period between minimum levels of pressure to determine duration of contraction. Then determination of changes in the ejection time from changes in duration of contraction will indicate exercise and a new ejection time typically a decreased ejection time indicating that the patient is engaging in exercise, will cause the microprocessor and/or other control circuitry of an implanted pacer to change the pacer rate.

Alternatively, impedance between two electrodes in the right ventricle can be measured continuously to determine changes in volume of blood in the right ventricle to determine opening and closing of the pulmonary valve to determine ejection time. Then changes in the ejection time, such as a decrease in ejection time, determined in the above manner, can be used to determine the appropriate pacer rate and the pacer rate can be adjusted accordingly. Also, from the foregoing description, it will be apparent that the apparatus 10 of the present invention and the method for using same described above have a number of advantages, some of which have been described above and others of which are inherent in the invention. In particular, the apparatus 10 allows an implanted pacer system to mimic a change in heart rate that would normally occur in a healthy heart when the individual is exercising and his heart is not naturally changing the pacing rate thereof due to some heart malfunction such as sinus node disease. Such apparatus or pacer system 10 will have very little time lag relative to the exercise activity and responds quickly to a need for a changed pacer rate.

Also it will be apparent that modifications can be made to the apparatus 10 and method for using same without departing from the teachings of the present invention. Accordingly, the scope of the invention is only to be limited as necessitated by the accompanying claims.

I claim:

1. An apparatus for pacing a heart in accordance with the heart/pacer rate needed to produce a required cardiac output while the person is exercising relative to ejection time of the right ventricle and changes thereof, comprising:

a demand pacer for implantation in a human body, said pacer having a pulse generator and control circuitry, which may be realized by a microprocessor, mounted therein;

a pacing lead for implantation in a heart, said lead including a lead body having a tip electrode adapted to engage and supply pacing pulses to a right ventricle of a heart;

sensing means mounted on said lead body for sensing changes in the right ventricle of the heart for determining the ejection time of the right ventricle and changes in ejection time over time in the right ventricle, such sensing including measurements selected from the group consisting of measurements of changes in volume of the right ventricle, measurements of changes in pressure in the right ventricle and measurements of changes in impedance of the fluid in the right ventricle; and said control circuitry including means for determining ejection time from the sensing of changes in the right ventricle and for relating ejection time and the changes in ejection time in the right ventricle with the required pacing rate and changes in the existing pacing rate needed to supply a desired cardiac output and for causing said pacer to pace the heart at the required rate when the heart is not naturally paced.

2. The apparatus of claim 1 wherein said means for sensing changes in the right ventricle includes pressure sensing means mounted on said pacing lead.

3. The apparatus of claim 2 wherein said pressure sensing means comprise a strain gauge mounted in said lead body and spaced from said tip electrode.

4. The apparatus of claim 2 wherein said pressure sensing means comprise a piezoresistive microelectronic pressure transducer mounted in said lead body and spaced from said tip electrode.

5. The apparatus of claim 2 wherein said means for determining ejection time includes means for relating changes in pressure over time to duration of contraction, which time period is related to ejection time.

6. The apparatus of claim 4 wherein said control circuitry includes a pulse generator and a microprocessor programmed to cause voltage pulses to be supplied from said pulse generator to said pressure transducer for pressure sampling to minimize the power drain of the pressure transducer on the power supply of the pacer.

7. The apparatus of claim 6 including means for supplying voltage pulses having a duty cycle of at least 1:200.

8. The apparatus of claim 1 wherein said means for sensing changes in the right ventricle includes two electrodes on said lead whereby impedance can be measured across said electrodes when a current is applied through said electrodes.

9. The apparatus of claim 8 wherein said two electrodes are defined by said tip electrode and a ring electrode on said pacing lead a sufficient distance behind said tip electrode so as to be able to be received in the right ventricle.

10. The apparatus of claim 1 wherein said means includes four electrodes, of which two electrodes are ring electrodes one positioned behind but spaced from said tip electrode and another ring electrode spaced a sufficient distance so as to be able still to be received in the right ventricle and said pacer has a casing which serves as the fourth electrode, whereby impedance can be measured between said two ring electrodes on the lead when a current is passed between the pacer casing and said tip electrode.

11. The apparatus of claim 10 wherein said ejection time determining means includes means for supplying current pulses from said control circuitry to said electrodes and, means for receiving voltage pulses from said two ring electrodes and for supplying same to said control circuitry, and means for determining impedance values from the voltage and the current pulses, for relating changes in impedance to changes in blood volume in the right ventricle and changes in blood volume to openings and closings of the pulmonary valve and for determining the time period between each opening and closing which is related to, if not equal to, ejection time.

12. The apparatus of claim 1 wherein said control circuitry includes a microprocessor and a memory, and said means for relating the right ventricular ejection time and/or changes thereof with the required pacer rate include an algorithm stored in said memory.

13. The apparatus of claim 12 wherein said microprocessor includes means for implementing said algorithm including means for:

determining the ejection time in the right ventricle at a point in time T;

computing the heart/pacer rate $R_T$ from a programmed slope "A" of a graph of heart rate versus ejection time between a minimum heart rate and a maximum heart rate;

determining whether the heart rate calculated is equal to or above the programmed maximum pacer rate or equal to or below the programmed minimum pacer rate; and if the calculated heart rate is at or above the programmed maximum pacer rate or at or below the programmed minimum pacer rate, replacing the pacer rate value stored in said memory with either the programmed maximum pacer rate or the programmed minimum pacer rate respectively; or if the calculated heart rate is between the programmed minimum pacer rate and the programmed maximum pacer rate, replacing the pacer rate value stored in the memory with the newly calculated rate in said memory;

replacing the ejection time value stored in said memory at time $T-1$ with the newly determined ejection time value; and altering the pacer rate of the pacer by the newly calculated rate.

14. The apparatus of claim 13 including means for programming in said microprocessor a family of slopes parallel to the first named slope whereby the implemented algorithm functions independent of a particular ejection time and in response to changes in ejection time so as to be substantially insensitive to any drift in the means for determining ejection time.

15. The apparatus of claim 12 wherein said memory has stored therein a look-up table of required pacing rates relative to various values of right ventricular ejection time and said microprocessor includes means for implementing said algorithm including means for:

determining the ejection time in the right ventricle;

looking up the corresponding heart rate in the look-up table; and monitoring and repeating the step of determining ejection time and changing the pacing rate as the pressure changes.

16. The apparatus of claim 12 wherein said memory has stored therein a look-up table of required heart rate changes relative to various values of right ventricular ejection time changes and said microprocessor includes means for implementing said algorithm including means for:

determining the ejection time at a first point in time;

computing the incremental change in ejection time $\Delta ET = ET_T - ET_{T-1}$; looking up the corresponding R in the look-up table;

computing the required heart rate $R_T = \Delta R + R_{T-1}$;

determining whether the computed heart rate is equal to or above the programmed maximum pacer rate or is equal to or below the programmed minimum pacer rate; and if the calculated heart rate meets either of these conditions, replacing the pacer rate $R_{T-1}$ by either the programmed maximum pacer rate or programmed minimum pacer rate stored in said memory and replacing the last determined ET value;

if the heart rate calculated is between the maximum and minimum pacer rates stored in said memory, replacing the last pacing rate by the newly computed rate and replacing the last ejection time value by the newly determined ejection time value; and adjusting the pacer rate to the value of the heart rate just calculated.

17. The apparatus of claim 16 including means for smoothing the heart/pacer rate changes by smoothing the changes in ejection time.

18. The apparatus of claim 16 including means for comparing the sign of the result of $\Delta ET_T = ET_T - ET_{T-1}$ to the sign of the N−1 previously computed differences which have been stored and if there is no sign change in N consecutive samples, means for causing the algorithm to determine the appropriate rate change, if the sign of the present increment $\Delta ET$ is equal to the sign of the previous N−1 increments, the algorithm increments another increment of $\Delta ET$ for the next comparison, and if the sign changes, the new sign is stored in the memory and the said microprocessor returns to the step of determining ejection time.

19. The apparatus of claim 16 including means for basing the rate change on the average value of $\Delta ET$ over the N most recent samples if no sign change has occurred.

20. A method for pacing a heart in accordance with the heart rate needed to produce a required cardiac output while a person is exercising and relative to ejection time in the right ventricle and changes thereof, comprising the steps of:

sensing changes in the right ventricle from about the end of right atrial systole through right ventricular systole during each heart cycle, such sensing including measurements selected from the group consisting of measurements of changes in volume in the right ventricle, measurements of changes in pressure in the right ventricle, and measurements of changes in impedance of the fluid in the right ventricle; determining ejection time ($E_2$ or $E_3$) and changes in ejection time in the right ventricle from the sensing of changes in the right ventricle;

relating ejection time ($E_2$ or $E_3$) and the changes in ejection time in the right ventricle with the required heart rate and change in heart rate needed to supply a desired cardiac output; and pacing the heart at the required heart rate when the heart is not naturally paced.

21. The method of claim 20 wherein said step of determining ejection time includes the steps of: measuring pressure in the right ventricle at short time intervals over time; determining changes in pressure; relating the pressure sensed over time and changes in pressure to the duration of contraction; determining the duration of contraction during the time the pressure increases and decreases; and determining each ejection time ($E_2$) from each said time period.

22. The method of claim 21 wherein pressure is sensed by a piezoresistive pressure transducer and said method includes the step of supplying voltage pulses to said pressure transducer for pressure sampling to minimize the power drain of the pressure transducer on a power supply for the transducer.

23. The method of claim 22 wherein said voltage pulses have a duty cycle of at least 1:200.

24. The method of claim 20 wherein said steps of sensing changes in the right ventricle and determining ejection time ($E_3$) includes the steps of:

determining blood volume and changes in blood volume in the right ventricle over time; relating the blood volume and changes in blood volume to openings and closings of the pulmonary valve; determining the time period between each opening and closing during the time period when the volume changes from a maximum value to a minimum value; and determining each ejection time ($E_3$) from each said time period.

25. The method of claim 24 wherein blood volume and changes in blood volume are determined by the steps of: measuring at short intervals over time the impedance between two electrodes in the right ventricle; and correlating the impedance measurements and changes in impedance with blood volume and changes in blood volume over time.

26. The method of claim 20 wherein said steps of relating the right ventricular ejection time and/or the time derivative therof with the required pacer rate comprises the steps of:

determining the ejection time in the right ventricle at a point in time T;

computing the heart rate $R_T$ from a slope "A" of a graph of heart rate versus ejection time between a programmed minimum pacer rate and a programmed maximum pacer rate;

determining whether the heart rate calculated is equal to or above the programmed maximum pacer rate or equal to or below the programmed minimum pacer rate; and if the calculated heart rate is at or above the programmed maximum pacer rate or at or below the programmed minimum pacer rate, replacing the pacer rate value stored in a memory with either the programmed maximum pacer rate or the programmed minimum pacer rate, respectively; or if the calculated heart rate is between the programmed minimum pacer rate and the programmed maximum pacer rate, replacing the pacer rate value stored in the memory with the newly calculated rate in the memory;

replacing the ejection time value stored in the memory at time T−1 with the newly measured ejection time value; and altering the pacer rate of the pacer by the newly calculated rate.

27. A method of claim 26 includes the step of computing the heart rate from a family of slopes parallel to the first named slope whereby said method is independent of a particular ejection time and alters pacer rate in response to changes in ejection time so as to be substantially insensitive to drift in any means used for determining ejection time.

28. The method of claim 26 wherein different slopes A, $A_1$, $A_2$, etc. are programmed in the microprocessor and said method includes the step of selecting a slope most closely related to the natural change in ejection for changes in heart rate for the patient.

29. The method of claim 20 wherein said step of relating the right ventricular ejection time with the required heart rate comprises the steps of:

determining the ejection time in the right ventricle;

looking up the corresponding heart rate in a look-up table of heart rates relative to various values of right ventricular systolic ejection time;

adjusting the pacer rate to the value looked up in the look-up table; and monitoring and repeating the step of determining ejection time and changing the pacing rate as the ejection time changes.

30. The method of claim 26 wherein said step of relating the right ventricular ejection time with the required heart rate comprises the steps of:

determining the ejection time at a first point in time;

computing the incremental change in ejection time, $\Delta ET = ET_T - (ET_{T-1})$;

looking up the corresponding changes in heart rate, $\Delta R$ in, a look-up table of heart rates relative to various values of right ventricular ejection time;

computing the required heart rate $R_T = \Delta R + (R_{T-1})$;

determining whether the computed heart rate is equal to or above the programmed maximum pacer rate or is equal to or below the programmed minimum pacer rate; and if the calculated heart rate meets either of these conditions, replacing the pacer rate $R_{T-1}$ by either the programmed maximum pacer rate or programmed minimum pacer rate stored in a memory and replacing the last sensed ejection time value with the newly sensed ejection time value;

if the heart rate calculated is between the programmed maximum and minimum pacer rates stored in the memory, replacing the last pacing rate by the newly computed rate and replacing the last ejection time value by the newly determined ejection time value; and adjusting the pacer rate to the value of the rate just calculated.

31. The method of claim 30 including the step of smoothing the heart/pacer rate changes by smoothing the changes in ejection time.

32. The method of claim 31 including the step of comparing the sign of the result, $\Delta ET_T = ET_T - (ET_{T-1})$ to the sign of the $N-1$ previously computed differences which have been stored and if there is no sign change in N consecutive samples, determining the appropriate rate change, if the sign of the present increment in ejection time $\Delta ET$ is equal to the sign of the previous $N-1$ increments in ejection time, incrementing another increment of ejection time $\Delta ET$ for the next comparison, and if the sign changes, storing the new sign in the memory and returning to the initial step of determining ejection time.

33. The method of claim 32 including the step of basing the rate change on the average value of $\Delta ET$ over the N most recent samples if no sign change has occurred.

* * * * *